US006736833B2

(12) United States Patent
Coleman (10) Patent No.: US 6,736,833 B2
(45) Date of Patent: May 18, 2004

(54) APPLICATION OF UV TO COLLAGEN FOR ALTERING LENGTH AND PROPERTIES OF TISSUE

(75) Inventor: Struan H. Coleman, New York, NY (US)

(73) Assignee: Hospital for Special Surgery, New York, NY (US)

(*) Notice: Subject to any disclaimer, the term of this patent is extended or adjusted under 35 U.S.C. 154(b) by 8 days.

(21) Appl. No.: 10/163,360

(22) Filed: Jun. 7, 2002

(65) Prior Publication Data

US 2002/0188335 A1 Dec. 12, 2002

Related U.S. Application Data (60) Provisional application No. 60/296,594, filed on Jun. 7, 2001.

(51) Int. Cl.$^7$ ............................................. A61N 5/01
(52) U.S. Cl. .............................. 607/94; 128/898; 606/9
(58) Field of Search ........................ 607/94, 88; 606/9, 606/10, 13; 128/898

(56) References Cited

U.S. PATENT DOCUMENTS 4,729,372 A * 3/1988 L'Esperance, Jr. ............ 606/5
5,683,366 A * 11/1997 Eggers et al. ................ 604/114
6,406,474 B1 * 6/2002 Neuberger et al. ............. 606/9
6,447,503 B1 * 9/2002 Wynne et al. .................. 606/9
6,511,475 B1 * 1/2003 Altshuler et al. .............. 606/9

OTHER PUBLICATIONS

Arnoczky, Steven P. and Aksan, Alptekin Thermal Modification of Connective Tissues: Basic Science Considerations and Clinical Implications, Journal of the American Academy of Orthopaedic Surgeons.

* cited by examiner

Primary Examiner—Lee Cohen
Assistant Examiner—H M Johnson, III
(74) Attorney, Agent, or Firm—Kramer & Amado, P.C.

(57) ABSTRACT

The present invention relates to the structural modification of human tissue comprising collagen by irradiation of tissue with UV photons. The present invention discloses methods of altering the structural and mechanical properties of the tissue by treatment of the tissue with thermal energy and/or UV photons. The present invention further discloses an apparatus for the treatment of tissues with thermal energy and/or UV photons.

15 Claims, 4 Drawing Sheets

FIG. 1

The effects of heat on bovine extensor tendon containing type I collagen (from Wall et al. 1999).

FIG. 2

The change in the modulus of elasticity of bovine extensor tendon as a function of thermal modification (from Wall et al., 1999).

FIG.3
The proposed structure of the type I collagen triple Helix.

FIG.4
Proposed pathways for the formation of stable and unstable collagen cross-links.

L.H.: Lysyl hydroxylase, L.O.: Lysyl oxidase, ACP: Aldol condensation product (*Intra* molecular cross-link), deH: dehydro
HLNL: hydroxylysinonorleucine, DHLNL: dihydroxylysinonorleucine, HHMD: histidinohydroxymerodesmosine
HHL: histidinohydroxylysinonorleucine, Pyr.: pyridinoline, d-Pyr: deoxypyridinoline, Pyrrl: pyrrole ☐ Reducible cross-links,   ▭ Nonreducible cross-links,   ( ) Tissue distribution

FIG.5
The proposed structure of the pyridinoline, heat stable cross-link between type I collagen triple helices.

FIG.6
The effects of Irradiation with UV photons in the wavelength range of 250 nm - 420 nm alone or thermal energy alone on the modulus of elasticity of bovine shoulder capsule *in vitro*.

FIG.7
The effects of a combination of Irradiation with UV photons in the wavelength range of 250 nm - 420 nm and thermal energy on the modulus of elasticity of bovine shoulder capsule.

FIG.8
The cross link analysis of bovine shoulder capsule treated with either UV irradiation of thermal energy or a combination.

* Denotes $p < 0.05$; N=12

APPLICATION OF UV TO COLLAGEN FOR ALTERING LENGTH AND PROPERTIES OF TISSUE

This application claims the benefit of U.S. Provisional Application No. 60/296,594 entitled "Application of UV to collagen for altering length and properties of tissue," filed on Jun. 7, 2001.

FIELD OF THE INVENTION

The present invention relates to the structural modification of human tissues containing collagen with ultraviolet (UV) irradiation.

BACKGROUND OF THE INVENTION

Collagen is an insoluble fibrous protein that is present in vertebrates as the chief constituent of connective tissue fibrils, articular cartilage, nucleus pulposus, and in bones. The collagen family represents a diverse group of extracellular matrix molecules that have a triple-helix structure. A single chain of collagen is defined as an α-chain. Each collagen molecule consists of three α-chains usually identical. The only known exception is Type I collagen. Type I collagen consists of two identical chains (α1) and one different chain (α2). It is the only heteropolymer among collagens. The three polypeptide chains are stabilized as a type II left handed triple helix by intramolecular bonds. The collagen triple helices are processed in the extra-cellular matrix and self-assemble into a fibrillar structure that is stabilized primarily by intermolecular bonds. The triple helix forms a rod-like structure that is important for fibril formation and structural integrity. In higher animals, at least 19 types of collagen have been identified. Type I collagen is the principal component of bone, skin, and tendon, and is the predominant type of collagen in a mature cicatrix (scar). Type II collagen is the major type found in cartilage.

The length and mechanical properties of tissues comprised primarily of type I collagen, such as ligaments, tendons intervertebral discs, and joint capsule, can become altered as a result of an injury or a disease process. Similarly, articular cartilage, comprised primarily of type II collagen, becomes softened in the early stages of osteoarthritis. Recently, thermal energy has been used to shrink lax or redundant tissue containing type I collagen (Hayashi et al. Am. J Sports Med, 1977, 25:107–112). Thermal energy has also been applied to articular cartilage in an attempt to "stiffen" damaged surfaces. Infrared (IR) laser energy and radio frequency (RF) energy, either unipolar or bipolar, are presently the two most common delivery systems used in humans for thermal modification of tissues containing collagen (Arnoczky and Aksan, J Am Acad Ortho Surg, 2001, 8:305–313). Thermal energy applied from such heat sources is thought to shrink tissue comprised of collagen by breaking heat-labile intramolecular and intermolecular bonds (such as hydrogen and Van deer Waals bonds), thereby denaturing the collagen from a highly organized pseudo-crystalline structure to a random, gel-like state (Flory and Garret, J Am Chem Soc, 1958, 80:4836–4845). Furthermore, unlike some other proteins, heat denatured collagen is unable to refold back to its organized structure.

Figure 1:
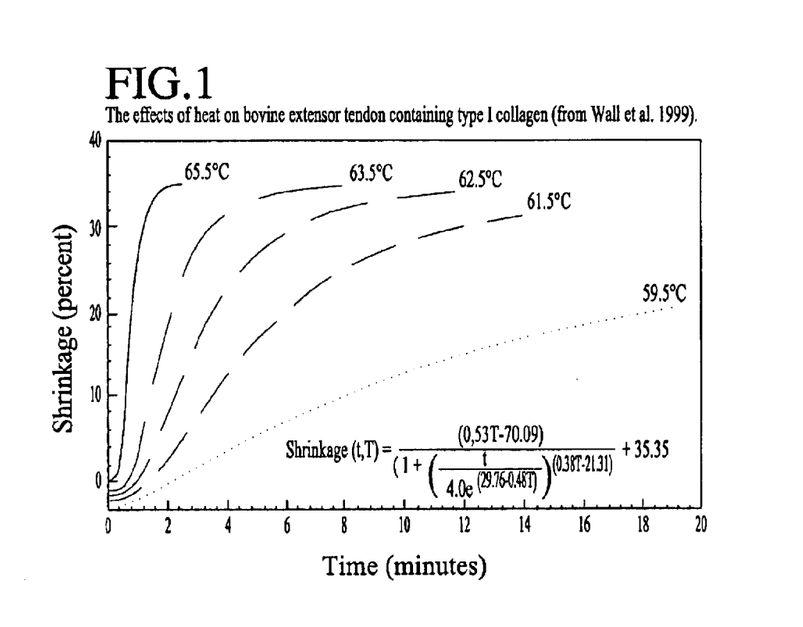
FIG. 1 is a graphic representation of the effects of thermal energy on the shortening of bovine extensor tendon containing type I collagen (from Wall et al., 1999).
Figure 2:
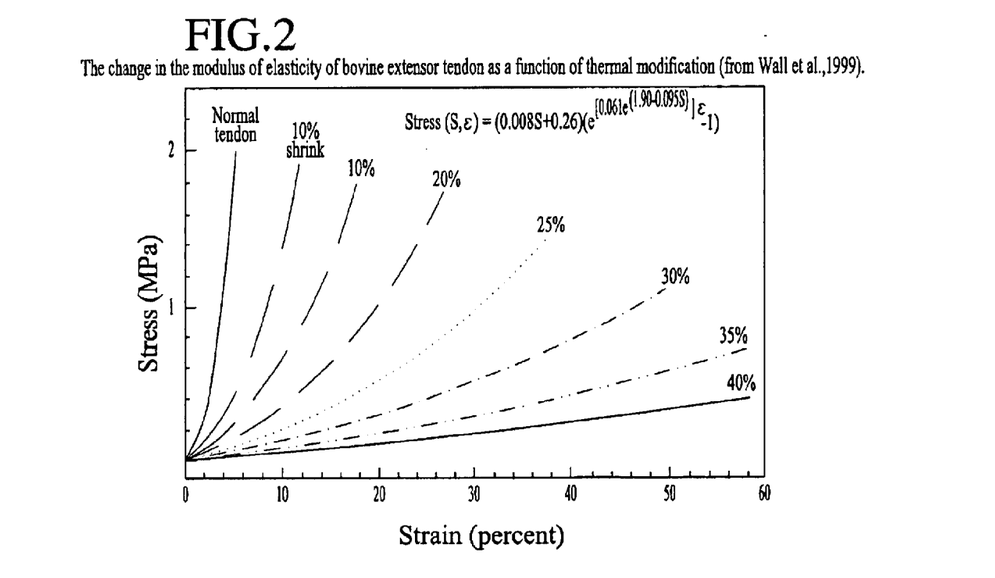
FIG. 2 is a graphic representation of the effects of thermal energy on the modulus of elasticity of bovine extensor tendon containing type I collagen (from Wall et al., 1999).
Figure 3:
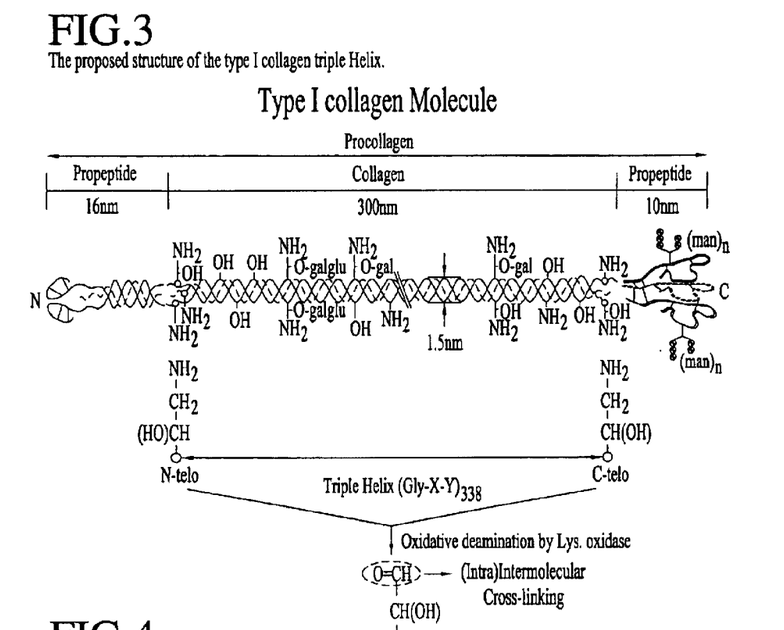
FIG. 3 is a proposed structure of the type I collagen triple helix prior to oxidative deamination by lysyl oxidase in the extra-cellular matrix.

However, while thermal denaturization shrinks tissue containing collagen, it also decreases the elastic modulus (modulus) of the treated tissue. Wall and co-workers demonstrated that for thermal denaturization of bovine extensor tendon, comprised primarily of type I collagen, shrinkage of the tissue is both temperature and time dependent (see FIG. 1) (Wall et al. J Shoulder Elbow Surg, 1999, 8:339–344). But, as illustrated graphically in FIG. 2, the modulus of thermally denatured tissue decreases as a function of the percent of tissue shrinkage.

Although the theory relating to such loss of modulus after thermal treatment is not fully understood, the mechanism of thermal denaturization of collagen might be partially understood by referring to its molecular structure (Brodsky and Ramshaw, Matrix Bio, 1997, 15:545–554). The application of thermal energy to collagen disrupts heat labile bonds (e.g. hydrogen bonds between the α chains) and causes the collagen triple helix to unwind, leaving the polypeptide chains in a denatured state.

Weakening of thermally denatured tissues containing collagen presents a serious clinical problem for patients in the immediate post-operative period. More specifically, tissue that has been shortened or smoothed by thermal denaturization is at risk to stretch out with any applied tensile force. Therefore, there is a continuing need in the art to develop methods to treat tissues that are too lax or too tight.

Thus it is an object of the present invention to provide a method for modifying tissue modulus of elasticity.

It is a further object of the present invention to provide an apparatus for modifying the mechanical properties of tissue.

It is still a further object of the present invention to provide an apparatus and a method for modifying tissue modulus of elasticity while maintaining the positive molecular and mechanical characteristics of non-thermally denatured tissues.

The foregoing objects and advantages of the invention are illustrative of those that can be achieved by the present invention and are not intended to be exhaustive or limiting of the possible advantages which can be realized. Thus, these and other objects and advantages of the invention will be apparent from the description herein or can be learned from practicing the invention, both as embodied herein or as modified in view of any variation which may be apparent to those skilled in the art. Accordingly, the present invention resides in the novel methods, arrangements, combinations and improvements herein shown and described.

SUMMARY OF THE INVENTION

In light of the present need for providing an efficient and reliable apparatus for performing a method for modifying tissue modulus of elasticity, a brief summary of the present invention is presented. Some simplifications and omission may be made in the following summary, which is intended to highlight and introduce some aspects of the present invention, but not to limit its scope. Detailed descriptions of a preferred exemplary embodiment adequate to allow those of ordinary skill in the art to make and use the invention concepts will follow in later sections.

The present invention contemplates a method for modifying tissue modulus of elasticity, where the method comprises the steps of (a) maintaining the temperature of the tissue within a selected temperature range, (b) providing UV photons at a predetermine wavelength or within a selected wavelength range, and (c) irradiating the tissue with a selected dose of UV photons at a predetermined intensity for a predetermined length of time. In one embodiment of the present invention, the method further comprises maintaining the pH of the tissue and/or adding at least one pharmaceutically acceptable free radical producing compound. In a further embodiment of the present invention, the method further comprises testing the tissues prior to the method. The steps of the present method may be performed in any order to produce the desired results. In a further embodiment of the present invention, the selected temperature may be either above the temperature required for denaturization of collagen within the tissue (e.g., from about 55 degrees C. to about 65 degrees C.) or below the temperature range required for denaturization of collagen within the tissue (e.g., from about 37 degrees C. to about 39 degrees C.). The UV photons may be delivered through a fiber optic cable. The present invention may be used on any tissues, such as joint capsule, tendon, ligament, fibrocartilage, hyaline cartilage, bone, skin and muscle. The wavelengths that may be used are preferably 250 nm–420 nm, more preferably 320 nm–390 nm.

The present invention also contemplates an apparatus for modifying mechanical properties of tissue. The apparatus may be comprised of a means for maintaining the temperature of the tissue, a means for generating UV photons at a selected wavelength and intensity; a means for irradiating the tissue with the UV photons; and a means for controlling the wavelength, the intensity, and the temperature. The present apparatus may further comprise a means for measuring the thickness and stiffness of the tissue.

The present invention also contemplates a method for increasing modulus of elasticity in a patient in need thereof, where the method comprises administering the method of the invention.

DETAILED DESCRIPTION OF THE INVENTION

The present invention contemplates a method and an apparatus for modifying the mechanical properties of tissues comprising collagen. Specific mechanical properties of the tissue that may be modified are the length of the tissue and the modulus of elasticity of the tissue. Examples of tissues that may be used in this method include, but are not limited to, a joint capsule, tendon, ligament, fibrocartilage, hyaline cartilage, intervertabral disc, bone, skin or muscle in an animal. Additionally, an apparatus for modifying the mechanical properties of tissue comprising collagen is contemplated.

As used herein, the term "UV irradiated" refers to tissues subjected to UV light. The light is comprised of UV photons. The term "UV photons" refers to a quantum of UV radiation. The UV light may be generated by any known methods (such as a lamp) and may be within any UV wavelength range. In a preferred embodiment, the wavelength range is from about 250 nm to about 420 nm.

As used herein, the term "thermal energy" refers to power that produces heat. As used within the application, a tissue may be subjected to thermal energy to alter the mechanical properties of the tissue. In a specific embodiment, tissue is subjected to thermal energy by a probe. The thermal energy may be produced by any known methods, such as infrared (IR) laser energy and unipolar or bipolar radio frequency (RF) energy.

As used herein, the phrase "collagen comprising tissue" refers to tissue sources that comprise collagen, which is an insoluble fibrous protein that is the chief constituent of connective tissue fibrils and in bones. In a specific embodiment, such tissues include joint capsule, tendon, ligament, fibrocartilage, hyaline cartilage, bone, skin or muscle. Preferably, the tissues are ligament and tendon.

The term "thermal denaturization" refers to breaking heat-labile intramolecular and intermolecular bonds (such as hydrogen and Van deer Waals bonds) in a protein. In specific embodiment, collagen is denatured. As used herein, the phrase "partially resistant to thermal denaturization" refers to tissues that have been previously treated to alter its mechanical properties. The previous treatment may have been surgical alterations or UV irradiation. These tissues then become less susceptible to the effects of thermal energy.

The phrases "modulus of elasticity" and "elasticity modulus" refers to a constant or coefficient that numerically expresses the degree to which a body or substance is elastic.

As used herein, "collagen denaturization temperature range" refers to the temperature needed to modify the molecular structure of collagen. The collagen may be isolated or within a tissue sources, such as a tendon. In a particular embodiment, the molecular structure of collagen is modified by cleaving heat-labile intramolecular and intermolecular bonds (such as hydrogen and Van deer Waals bonds).

The term "mechanical properties" refers to mechanical qualities or traits belonging to a specific tissue. For example, the ability of a tissue to stretch and bend. These traits may be dependent upon the structure of the collagen within the tissue.

The term "dose", as used herein, refers to the formula of intensity of UV provided over a specific time period. The dose provided to a patient or subject further depends upon the medium which the UV photons pass through. More specifically, if UV photons are required to pass through a physiological solution to reach the target tissue the dose provided to the patient may be different than when the photons are required to only pass through air. One of ordinary skill in the art would be able to determine these factors to provide the appropriate dose of UV photons to the tissue.

Methods for Modifying Mechanical Properties of Tissues Comprising Collagen

One embodiment of the present invention provides a method for modifying tissue comprised of collagen. The modifications include altering the tissue length and the modulus of elasticity by the application of ultraviolet (UV) light to the tissue. Other cross-linking agents, such as methylene blue, hydrogen peroxide and ozone; may be used in conjunction with UV light treatment to further increase the strength of the tissue. The present invention may be used on tissues such as joint capsule, tendon, ligament, fibrocartilage, hyaline cartilage, intraverterbral disc, bone, skin or muscle. The tissues may be in or from an animal or human.

In one embodiment of the present invention, a method comprising the steps of (a) maintaining the temperature of a tissue within a selected temperature range, (b) providing UV photons at a selected wavelength or within a selected wavelength range, and (c) irradiating the tissue with the selected dose of UV photons is disclosed. The present method may further comprise maintaining the pH of the tissue within a selected range, addition of at least one water soluble free radical producing compound, and/or pre-treatment and post-treatment testing of the tissue to assess physical and mechanical properties of the tissue (e.g., thickness of tissue and modulus of elasticity). The steps of the method may be repeated as necessary to achieve the desired effect. Additionally, the steps may be performed in any order to produce the desired effect (e.g., step (a) then step (b) then step (c) or step (b) then step (c) then step (a)). The tissue irradiated in the present method may be rendered partially resistant to thermal denaturization by the UV photons.

When tissue is UV irradiated in combination with thermal energy, the properties of the tissue are modified in a manner that is dependent upon the order of the treatments. For example, when thermal energy alone is applied to the tissue in the range required to denature collagen, the tissue is shortened and the modulus of elasticity of the tissue decreases. When tissue only is UV irradiated, the tissue shortens, as described above, the modulus of elasticity increases, and the tissue unexpectedly is rendered partially resistant to subsequent thermal denaturization. Thermally denatured tissue that is subsequently UV irradiated produces tissues that shrinks more and has a lowed modulus of elasticity than observed in tissues that are treated with heat or UV irradiation alone. When tissue containing collagen is UV irradiated and the temperature of the tissue is maintained at a range above that required for collagen denaturization, the tissue shortens and the modulus of elasticity increases. Interestingly, the length of the tissue and the modulus of elasticity tissue may increase by manipulation (Discussed below). When tissue contain collagen is UV irradiated and then treated with heat, the length of the tissue decreases and the modulus of elasticity does not change significantly.

Temperature

In one embodiment of the present invention, the tissue can be maintained at a selected temperature range. The temperature may be maintained by any method know in the art such as, but not limited to, a infrared wavelength, radiofrequency, a water bath, a heating pad, or with sterile saline with a pump for continuous inflow and outflow. In a specific embodiment, the temperature is maintained with heated, sterile saline that is pumped in and around the tissue. Specifically the temperature may be above or below the temperature needed to denature collagen (collagen denaturization temperature range) of the tissue. As discussed herein, collagen denatures at temperatures above 37 degrees C. One skilled in the art would maintain the temperature of the tissue below what is required for cutting and ablating the tissue. The temperature would depend on the modification to the tissue that is desired. For example, if it is desired to decrease the length of a tissue while increasing the elasticity, it is preferred to maintain the temperature near to or below the collagen denaturization temperature.

In one embodiment of the present invention, the temperature of the tissue is maintained at a temperature below the collagen denaturization temperature range for the tissue. Preferably, the temperature at which the tissue is maintained is at or below 37 degrees C.

In an alternative embodiment, the temperature of the tissue is maintained at a temperature where collagen denatures. Preferably, the temperature is above 37 degrees C. More preferably, the temperature is from 55 to 65 degrees C.

UV Irradiation

The tissue is irradiated with UV photons generated by an external source. The photons may be generated by any source known, such as a UV lamp containing a mercury-halogen bulb. A filter may be placed over the photon-generating source to deliver a specific UV wavelength or UV light within a specific wavelength range. Preferred wavelength ranges are between 250 nm and 420 nm and at a wavelength between 320 nm and 390 nm. Alternatively, a nitrogen laser may be used. Additionally, the UV photons may be delivered to the tissue by any method known, such as through a probe that contains a fiber optic cable. Once the photons are generated, they may be administered to the tissue source through the probe. After the tissue is treated, the tissue may be manipulated by hand (e.g., manual stretching of the tissue) in order to produce the required effects.

The distance between the probe and the tissue may be maintained or altered to modify the intensity of the UV irradiation. The time of treatment is dependent upon the required modification. Preferably, the tissue is treated with a specific dose of UV photons (intensity of UV photons x time of treatment). The dose used is dependent upon the modification required.

The wavelength or wavelength range used is dependent upon the modification required. The wavelength used will preferably not mutate proteins or DNA present in the tissue and will not heat the tissue that is being irradiated. Preferably, the wavelength range is from about 250 nm to 420 nm, more preferably the wavelength range is from about 320 nm to 390 nm.

pH

In addition to maintaining the temperature of the tissue, the pH of the selected tissue also may be controlled. The pH may be adjusted to alter the wavelength needed to modify collagen within the tissue source. For example, pyridinoline (a crosslinking amino acid in collagen) bonds are degraded at 275 nm when the pH is below 4 and degraded at 325 when the pH is above 4 (Sakura and Fujimoto, Can J Biochem, 1982, 60:525–529). Therefore, altering pH may allow one to modify specific bonds within collagen while not modifying other bonds. The pH of the tissue may be maintained by placing it in a solution where the pH has been adjusted to be in the desired range. For example, a solution comprised of physiological salts and where the pH has been altered with an acid or base (e.g., HCl or NaOH, respectively) may be used. The pH of the tissue preferably is maintained at a physiologic pH (ca. 7.4).

Free Radical Producing Compound

At least one pharmaceutically acceptable water-soluble free radical producing compound also may be added. The pharmaceutically acceptable compounds may be added to normal saline used for arthroscopic surgery. These pharmaceutically acceptable compounds may be added to further increase the stiffness and modulus of elasticity of the treated tissue. The pharmaceutically acceptable water-soluble free radical producing compounds encompass any such known compounds in the art. Such compounds include, but are not limited to methylene blue, hydrogen peroxide and ozone.

Testing of Tissues

The tissue may be tested before and/or after treatment with the method of the present invention. The testing may be used to empirically determine the dose needed for the tissue or may be used to determine if the tissue needs further treatment to produce the desired effect. For example, the thickness of the tissue may be measured using ultrasound. Determination of the thickness may be used to assess the necessary dose or if manual manipulation is needed to lengthen the tissue. Alternatively, a probe with a load cell may be used to assess stiffness of the tissue. Specifically, the probe may comprise a load cell that is pressed onto the tissue. The stiffness may indicate the dose needed or if further treatments are necessary.

Apparatus for Modifying Mechanical Properties of Tissues Comprising Collagen

An apparatus for modifying the mechanical properties of tissue comprising collagen is contemplated. The apparatus may be comprised of (1) a means for generating UV photons at a selected wavelength and intensity; (2) a means for irradiating the tissue with the UV photons; and (3) a means for controlling the wavelength. The apparatus further may comprise a means for measuring the thickness and stiffness of the tissue.

For example, the apparatus may comprise an arthroscopic probe that will be used to assess the state of the tissue and a fiber optic cable that will deliver the UV photons. The probe is inserted into the tissue through a small arthroscopic portal hole. Specifically, the apparatus comprises a load cell. The load cell is pressed onto the tissue to assess the stiffness of the tissue. After assessment, a filter may be selected on the external source or on the probe to limit the wavelength or wavelengths administered to the tissue. Additionally, the apparatus may comprise a heating device for arthroscopic surgery. Heating devices as produced by Arthrocare of Sunnyvale, Calif. (ArthroWands) and Oratec of Menlo Park, Calif. (ElectroTherma® Arthroscopy Systems) may be incorporated into the apparatus. These heating devices are radio frequency, bipolar devices. A lower power setting may be used to shrink tissue and sculpt cartilage whereas a higher setting may be used to ablate tissue. The apparatus of the present invention may also include a temperature sensor, an optical and illumination fiber as well as auxiliary lumens for other applications, such as suction or infusion of fluids.

Clinical Applications

The method of the present invention may be used in any situation where modification of collagen tissues is required. The method may be administered to any animal in need of tissue length modification treatment and/or alteration in the modulus of elasticity, including, but not limited to humans, primates, equines, bovines, canines, and felines. The principal tissues treated and/or tested in mammals are tendons, ligaments, and joint capsules; although the invention is not limited to use with such tissues and may be employed with any collagen containing tissues. Examples of human tissues with which the invention may be employed are fibrocartilage, hyaline cartilage, bone, and skin.

Clinical applications for the present invention include, by way of non-limiting examples, shortening and/or increasing the strength of a lax shoulder joint capsule; shortening and/or increasing the strength of a partially injured anterior cruciate ligament (ACL) or Achilles tendon; strengthening articular cartilage in the setting of early osteoarthritis or injury; strengthening a herniated nucleus pulposa and annulus fibrosa in the spine; weakening and lengthening capsular tissue around a contracted knee joint; and weakening and lengthening a flexor tendon in the hand that has a Dupytren contracture. All of these procedures can be performed arthroscopically or through a small skin incision in vivo.

One specific application of the present method may be in the treatment of an anterior cruciate ligament (ACL) in the knee that has been stretched out by an injury. The ACL does not heal on its own and a ligament graft is generally used to treat the injury. Currently, there are about 150,000 such ligament grafts that are performed each year in the US. Previous attempts to treat partial ACL tears (i.e. shorten the ligament) with only thermal energy have failed. It is proposed that even though the heat-treated ligament may have gotten shorter, it also was rendered weaker and unlike other tissues, such as the shoulder capsule, there is very little scar formation in the ACL. Consequently, the ligament stretches right out and probably longer than the pre-treatment length. This situation is an ideal one for UV treatment where the ligament can simultaneously be shortened and have its strength increased.

Clinical Methods

In the case of a lax shoulder joint capsule, arthroscopy is performed using sterile saline with a pump for continuous inflow and outflow. The continuous flow allows for clear visualization of the joint and also maintains the tissue at a desired temperature throughout the treatment. An arthroscopic camera is introduced through a standard posterior shoulder portal for visualization of the joint, and an arthroscopic probe is introduced through a standard anterior shoulder portal. The joint is inspected and the lax capsular tissue is identified with the probe. The probe is removed and a fiberoptic cable connected to a UV source is substituted through the anterior shoulder portal. The UV source is set to a selected intensity for a selected period of time and a selected wavelength that can be calibrated from test data measured in vitro such as described above. The UV source is turned on and the fiberoptic cable is moved over the lax capsule, while maintaining the temperature, until an effect is visualized with the camera. The probe is reintroduced to determine the effect of the UV radiation on the tissue. Once the surgeon is satisfied with the decreased length and the increased stiffness of the tissue, the probe and the camera are removed from the joint and the wounds are closed in the standard fashion.

In another example, a knee contracture also is treated arthroscopically using normal saline with continuous inflow and outflow. An arthroscopic camera is introduced into the knee joint through a lateral infrapatellar portal and a probe is introduced through a medial infrapatellar portal. A continuous outflow canula is placed in a lateral suprapatellar portal. Tight structures are identified with the probe and a fiberoptic cable with an incorporated heat source is introduced into the knee. The tight structures are first treated with thermal energy and are then irradiated with UV photons at a selected intensity for a selected period of time and a selected wavelength in order to weaken the tissue. The knee is then moved while the patient is still under anesthesia in order to lengthen the tight structures surrounding and within the joint capsule. Once the knee is sufficiently lax the arthroscopic devices are removed from the knee joint.

EXAMPLES

The present invention will be better understood by reference to the following Examples, which are provided as exemplary of the invention, and not by way of limitation.

Example I

Figure 4:
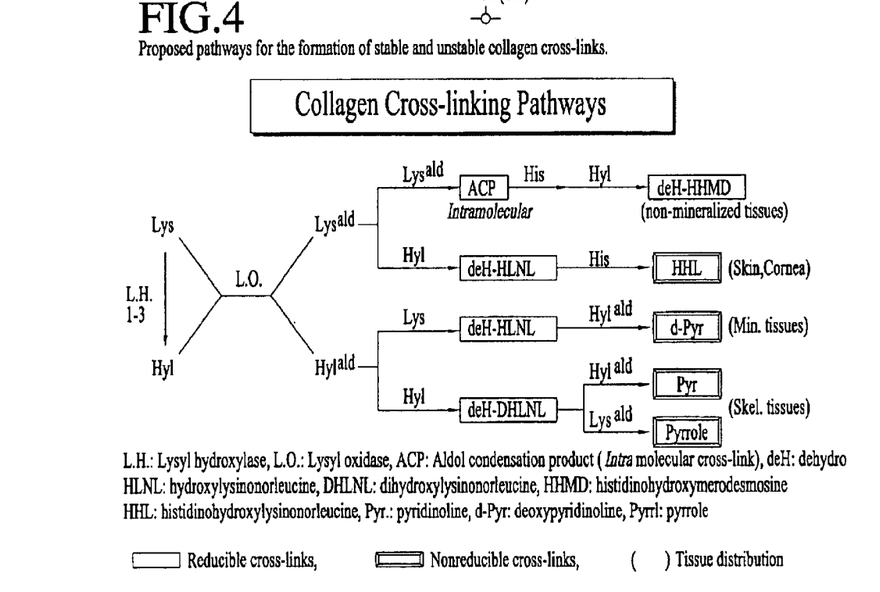
FIG. 4 is a proposed biochemical structure for the stable cross-link pyridinoline between two type I collagen triple helices.
Figure 5:
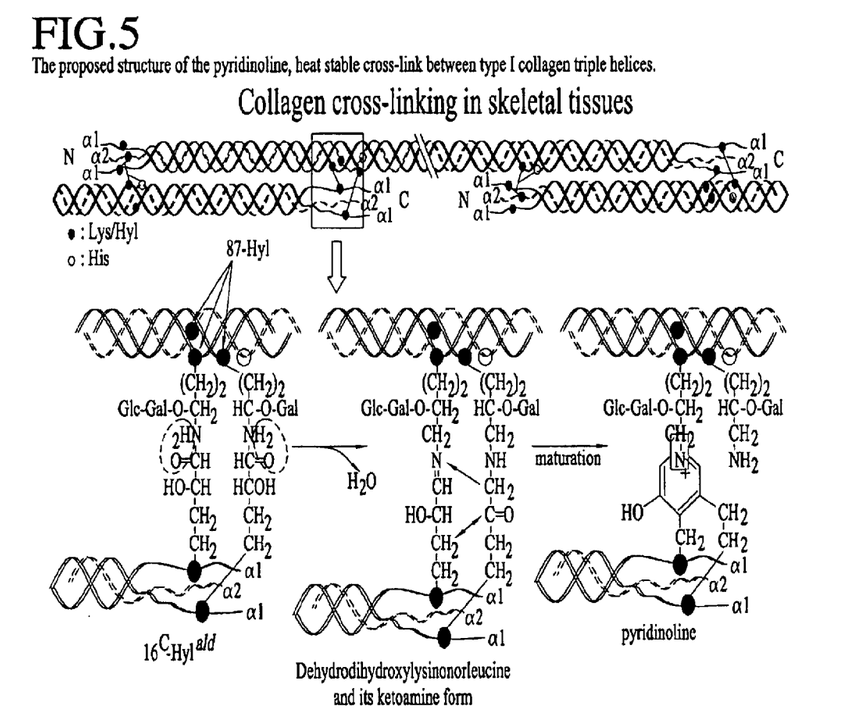
FIG. 5 depicts the proposed pathways for some of the intermolecular and intramolecular cross-links within the type I collagen molecule.

Bond concentration analysis on treated bovine shoulder capsule using high performance liquid chromatography (HPLC). We analyzed the absolute concentration of both heat stable and heat labile bonds in such capsule following three different treatment protocols: UV irradiation alone, UV irradiation followed by treatment with thermal energy and thermal energy alone. The heat labile bonds analyzed were hydroxylysinonorleucine (HLNL), dihydroxylysinonorleucine (DHLNL) and histidinohydroxymerodesmosine (HHMD), the pathways of which are shown in FIG. 4. FIG. 5 depicts the formation and structure of the pyridinoline bond, which is thermally stable at collagen denaturization temperatures. Isolated pyridinoline is known to absorb at 325 nm in neutral pH and at 295 nm in an acidic environment; the pyridinoline bond fluoresces at 395 nm. Photolysis of such isolated pyridinoline has been demonstrated at the two wavelengths, 295 nm and 325 nm, depending upon the pH of the solution.

Results

1. UV irradiation alone:
   DHLNL: No change; HLNL: No change; HHMD: 2–3-fold increase; Pyridinoline: No change
2. UV irradiation followed by thermal energy:
   DHLNL: No change; HLNL: 2-fold decrease; HHMD: No change; Pyridinoline: 5-fold decrease
3. Thermal energy alone:
   DHLNL: 2-fold decrease; HLNL: 2-fold decrease; HHMD: No change; Pyridinoline: 2-fold increase Based on the biomechanical findings and this bond analysis it was hypothesized that at temperatures below those required for denaturization, UV irradiation alters the structure and mechanical properties of the collagen molecule by cleaving UV sensitive, intermolecular pyridinoline cross-links between the collagen triple helices while preserving the collagen triple helical structure and, thereby, causing the triple helices to readjust their relative positions, thus shortening the tissue. The pyridinoline bonds then reform with the triple helices in a shortened position relative to one another.

In addition, UV irradiation was found to increase the concentration of HHMD bonds, which indicates UV induced cross-linking. HHMD cross-links involve four amino acid residues. The observed increase in HHMD bond concentration with UV irradiation may account for the increase in the modulus of treated tissues. Such HHMD cross-links also may be partly responsible for the resistance to thermal denaturation seen in UV irradiated tissue.

In contrast, thermal energy affects the structure of the collagen molecule by breaking the intramolecular hydrogen bonds and unwinding the collagen triple helices, which partially refold into a random, gel-like state. Thermal energy was also found to decrease the concentration of the heat labile bonds DHLNL and HLNL in the tissue, which may account for the decreased modulus observed in thermally denatured tissue containing collagen. Unexpectedly, thermal treatment alone of tissue comprised of collagen increases the concentration of pyridinoline bonds, although as discussed above, the modulus of such thermally denatured tissue substantially decreases. Furthermore, unlike UV irradiation at temperatures below those required for collagen denaturization, subsequent UV irradiation of thermally denatured tissue appears to break the heat stable pyridinoline bonds such that they are unable to reform; this decrease in pyridinoline concentration may account for the observed shortening and significant decrease in the modulus of tissue treated with this combined procedure. Thus, such application of UV irradiation, while maintaining a selected temperature and pH, is able to affect the length and mechanical properties of tissue comprised of collagen.

A previous attempt to strengthen collagen by irradiating with an unfiltered UV light source has been made by Weadock and associates; however, important differences exist between Weadock's work and the present invention. Weadock used a 1% dispersion of type I collagen that was isolated from bovine tissue, blended, centrifuged and extruded as a "synthetic" fiber, in contrast to the intact shoulder capsule used in the present work. In addition, Weadock used a UV cross-linking chamber that does not control for the wavelength of the light source or, most importantly, for the temperature of the sample. Finally, Weadlock disclosed that both the modulus and the ultimate tensile strength of his isolated, extruded collagen fibers increased with dehydrothermal treatment alone.

Example II

Bovine shoulder capsules were harvested and prepared for UV irradiation, treatment with thermal energy or a combination thereof, and for subsequent mechanical and biochemical analysis. Each capsule was sectioned into uniform strips of tissue; the cross-sectional area was calculated for each strip using digital calipers. The strips were secured between two clamps: one clamp was connected to a motor and the other clamp was connected to a load cell. Two marks were placed on the specimen in order to determine strain. The specimens were submersed in a water bath with external heating and with continuous flow in order to control and maintain the temperature of the specimen during treatment. A thermocouple probe was placed into the specimen for temperature monitoring. The temperature was maintained at about 37 degrees C. during UV irradiation and at temperatures within the range to cause denaturization of collagen for thermal energy treatments (e.g. 55 degrees C. to 65 degrees C.).

Once prepared, specimens were treated with UV irradiation alone, with thermal energy alone or with a combination of the two modalities. Two different filters were used to deliver photons in the UV wavelength: 250–420 nm and 320–390 nm. The UV photons were delivered from a commercially available mercury-halogen bulb (EFOS, Canada) through a fiber optic probe. The intensity of the UV irradiation and the distance between the tip of the probe and the target tissue were held constant throughout the experimentation.

In order to determine the amount of shrinkage for each specimen, a constant load was maintained during treatment and the change in distance between the two marks was recorded. Tissue shrinkage was calculated as a percentage of the original length of the specimen. Specimens were allowed to shorten either 5% or 10%. Specimens were then preloaded and cycled. A load/deformation curve was determined for each specimen prior to and after each treatment. Stiffness was calculated as the slope of the load/deformation plot. A stress/strain curve was also calculated for each specimen using cross-sectional area, and the modulus of elasticity was likewise calculated from the slope of the stress/strain plot.

Results

Figure 6:
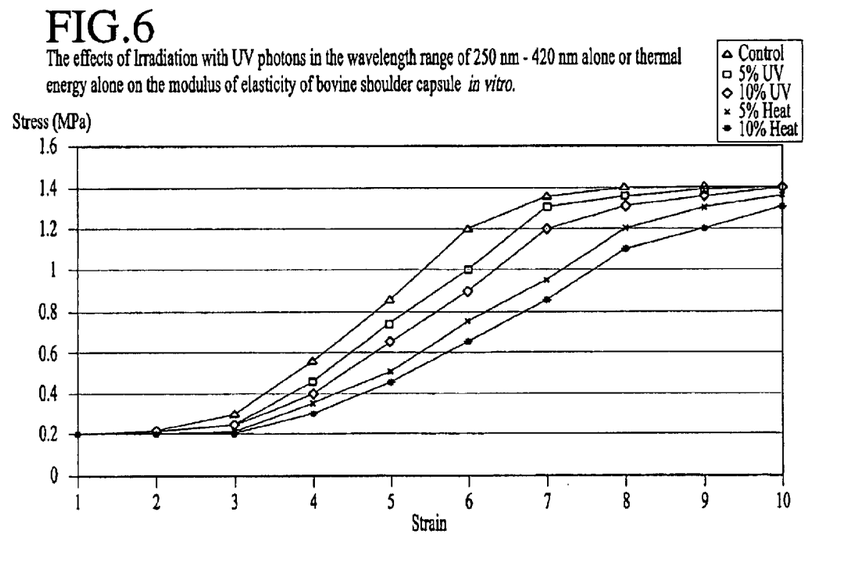
FIG. 6 is a graphic representation of the effects of either UV irradiation in the wavelength range of 250 nm–420 nm or thermal energy on the modulus of elasticity of bovine shoulder capsule in vitro.

FIG. 6 illustrates the change in the material properties of bovine shoulder capsule as a result of two different treatment modalities: UV irradiation alone in the wavelength range of 250 nm–420 nm and thermal denaturization alone. Different specimens were allowed to shorten about 5% and 10% for both treatments. In the case of thermal denaturization, specimens that were shortened by about 5% demonstrated a decrease in the modulus of the tissue compared to the same tissue prior to treatment. There was a further decrease in the modulus of tissue shortened by about 10% with thermal denaturization. In contrast, the modulus of elasticity was increased for specimens shortened by about 5% and 10% with UV irradiation alone with temperatures maintained below the collagen denaturization range (e.g. 37–39 degrees C.).

Figure 7:
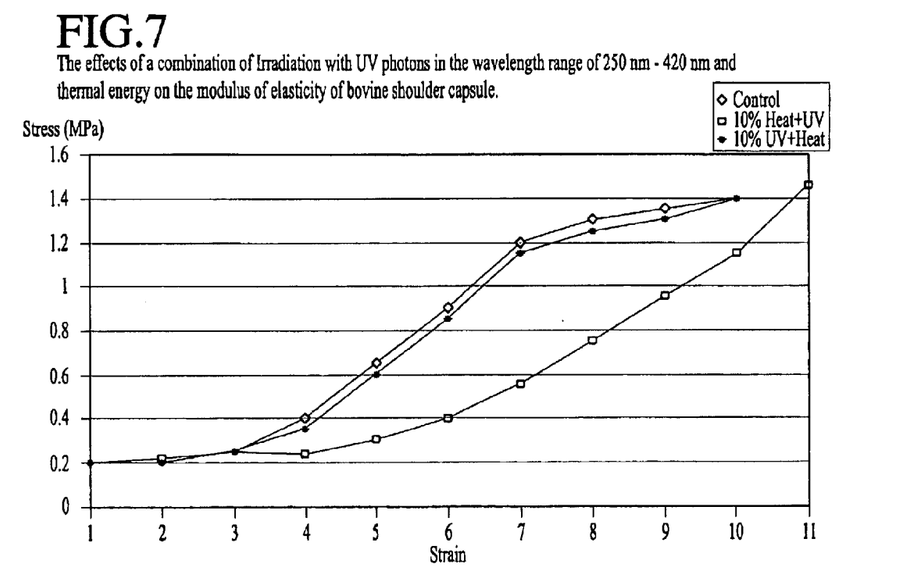
FIG. 7 is a graphic representation of the effects of a combination of UV irradiation in the wavelength range of 250 nm–420 nm and thermal energy on the modulus of elasticity of bovine shoulder capsule in vitro.
Figure 8:
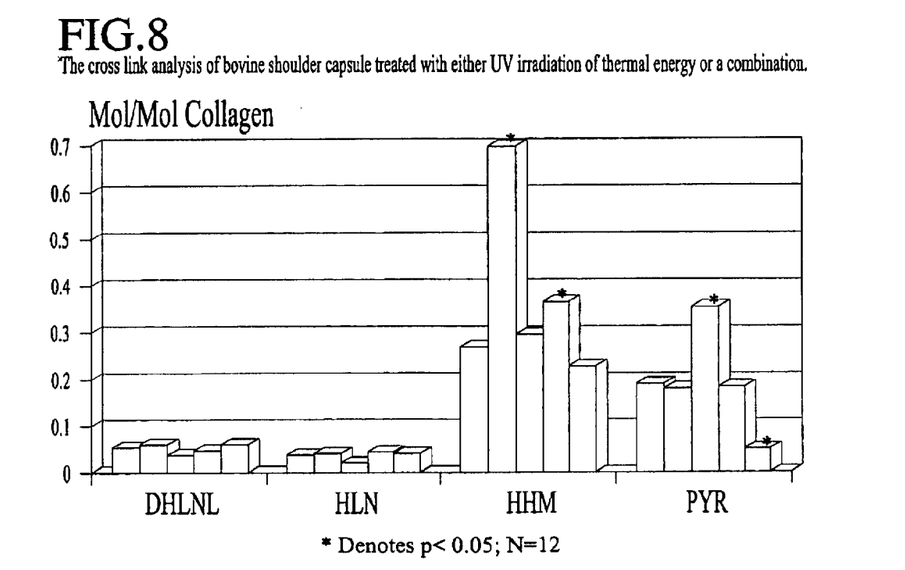
FIG. 8 is a crosslink analysis of bovine shoulder capsule treated with either UV irradiation of thermal energy or a combination.

FIG. 7 graphically illustrates the change in the material properties of bovine shoulder capsule after UV irradiation in the wavelength range of 250 nm–420 nm and subsequent treatment with thermal energy. As shown in FIG. 7, bovine capsule that was shortened by about 10% by UV irradiation demonstrated an increase in the modulus of the tissue. Subsequent treatment of UV irradiated bovine shoulder capsule with thermal energy shortened the tissue an additional 10%; however, this tissue demonstrated a resistance to shrinkage beyond about 10% and, furthermore, the modulus of the tissue only decreased to that of the untreated capsule. The shrinkage of bovine shoulder capsule treated by combined UV irradiation and subsequent thermal energy appears to lose the time and temperature dependence that is seen with thermal energy treatment alone.

FIG. 7 also graphically demonstrates the change in the material properties of thermally denatured bovine shoulder capsule after subsequent UV irradiation in the wavelength range of 250 nm–420 nm. Shortening the specimen by about 5% with thermal energy resulted in a decrease in the elastic modulus of the tissue compared to untreated specimens. Subsequent UV irradiation shortened the tissue more by about 10% and the modulus of the tissue decreased significantly. Furthermore, there was an increased rate of tissue shrinkage as a result of this combined treatment (thermal energy followed by UV irradiation) compared to treatment with either UV irradiation alone or thermal energy alone.

Example III

Arthroscopy is performed on the tissue to be treated using sterile saline with a pump for continuous inflow and outflow. The continuous flow will allow for visualization of the tissue and will maintain the tissue at a desired temperature. An arthroscopic camera is introduced for visualization of the tissue, and an arthroscopic probe is introduced and the lax tissue is identified with the probe. The probe is removed and the apparatus comprised of a fiberoptic cable connected to an external UV source is inserted. The UV source is set to a selected intensity for a selected period of time and a selected wavelength. The UV source is turned on and the apparatus is moved over the lax tissue, while maintaining the temperature, until an effect is visualized with the camera. The probe is reintroduced to determine the effect of the UV radiation on the tissue. Once the surgeon is satisfied with the result, the probe and the camera are removed from the tissue and the wounds are closed in the standard fashion.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that values are approximate, and are provided for description.

What is claimed is:

1. A method for modifying tissue modulus of elasticity, comprising:
   (a) maintaining the temperature of a tissue below the temperature range required for denaturization of collagen within the tissue,
   (b) providing UV photons at a predetermined wavelength or wavelength range, and
   (c) irradiating the tissue with said UV photons at a predetermined intensity for a predetermined length of time.

2. The method of claim 1, wherein the modulus of elasticity of the tissue is increased.

3. The method of claim 1, further comprising performing at least one of the following steps:
   (a) maintaining the pH of the tissue within a predetermined range, and
   (b) adding at least one pharmaceutically acceptable free radical producing compound.

4. The method of claim 1, wherein the method further comprises testing the tissues prior to the method.

5. The method of claim 1, wherein the steps are performed in the order of step (b), then step (c), and then step (a).

6. The method of claim 1, wherein the temperature is above the temperature required for denaturization of collagen within the tissue.

7. The method of claim 6, wherein the temperature is from about 55 degrees C. to about 65 degrees C.

8. The method of claim 1, wherein the temperature is from about 37 degrees C. to about 39 degrees C.

9. The method of claim 1, wherein the UV photons are delivered to the tissue through a fiber optic cable.

10. The method of claim 1, wherein the tissue is selected from the group consisting of joint capsule, tendon, ligament, fibrocartilage, hyaline cartilage, bone, skin and muscle.

11. The method of claim 1, wherein the predetermined wavelength range is 250 nm–420 nm.

12. The method of claim 1, wherein the predetermined wavelength range is 320 nm–390 nm.

13. An apparatus for modifying mechanical properties of tissue, the apparatus comprising:
   (a) means for generating UV photons at a selected wavelength and intensity;
   (b) means for irradiating the tissue with said UV photons;
   (c) means for controlling the temperature of the tissue below the temperature range required for denaturization of collagen within the tissue; and
   (d) means for controlling at least one of said wavelength and intensity.

14. The apparatus of claim 13 further comprising means for measuring the physical characteristics of the tissue.

15. A method for modifying tissue length, comprising:
   irradiating collagenous tissue with UV photons;
   said method performed using an apparatus, comprising:
   (a) means for generating UV photons at a selected wavelength and intensity;
   (b) means for irradiating the tissue with said UV photons;
   (c) means for controlling the temperature of the tissue below the temperature range required for denaturization of collagen within the tissue; and
   (d) means for controlling at least one of said wavelength and intensity.

* * * * *

UNITED STATES PATENT AND TRADEMARK OFFICE
CERTIFICATE OF CORRECTION

PATENT NO.    : 6,736,833 B2
DATED         : May 18, 2004
INVENTOR(S)   : Struan H. Coleman et al.

It is certified that error appears in the above-identified patent and that said Letters Patent is hereby corrected as shown below:

<u>Title page,</u>
Item [75], Inventors, after "(US)" please insert -- Russell F. Warren, Greenwich, CT (US), Peter A. Torzilli, Ridgefield, CT (US) --

Signed and Sealed this

Twenty-first Day of December, 2004

JON W. DUDAS
*Director of the United States Patent and Trademark Office*